United States Patent [19]
Koenigsberg et al.

[11] Patent Number: 4,989,942
[45] Date of Patent: Feb. 5, 1991

[54] COLLIMATED LIGHT OPTRODE

[75] Inventors: Harold M. Koenigsberg, Beverly Hills; Dan J. O'Neal, Hermosa Beach, both of Calif.

[73] Assignee: Hughes Aircraft Company, Los Angeles, Calif.

[21] Appl. No.: 413,497

[22] Filed: Sep. 27, 1989

[51] Int. Cl.$^5$ .............................. G02B 6/32
[52] U.S. Cl. .................. 350/96.18; 350/96.2; 250/573; 250/576; 356/436
[58] Field of Search ............ 350/96.1, 96.15, 96.18, 350/96.2, 96.29; 250/573, 576; 356/436

[56] References Cited

U.S. PATENT DOCUMENTS

| | | | |
|---|---|---|---|
| 4,398,791 | 8/1983 | Dorsey | 350/96.18 |
| 4,629,903 | 12/1986 | Giacobbe et al. | 250/573 |
| 4,730,891 | 3/1988 | Poorman | 350/96.18 |
| 4,752,131 | 6/1988 | Eisenlauer et al. | 250/573 |
| 4,842,355 | 6/1989 | Gold et al. | 350/96.18 |

FOREIGN PATENT DOCUMENTS 2934099  3/1981  Fed. Rep. of Germany ...... 250/573

Primary Examiner—John D. Lee
Assistant Examiner—John Ngo
Attorney, Agent, or Firm—Leonard A. Alkov; Wanda K. Denson-Low

[57] ABSTRACT

Light generated by an illumination source (26) travels through a fiber optic cable (40) to optrode (14) which is immersed in the process fluid (16) to be analyzed. The optrode collimates the light beam before it crosses the sampling gap (68) where the beam transects the process fluid to be analyzed. As it crosses the sampling gap 68, the light beam is absorbed in a specific wavelength band by the chemical species in solution. The collimated beam is then picked up by an opposing collimated lens in the optrode and transmitted to the protected analytical module (20) by a second optical fiber (42).

20 Claims, 2 Drawing Sheets

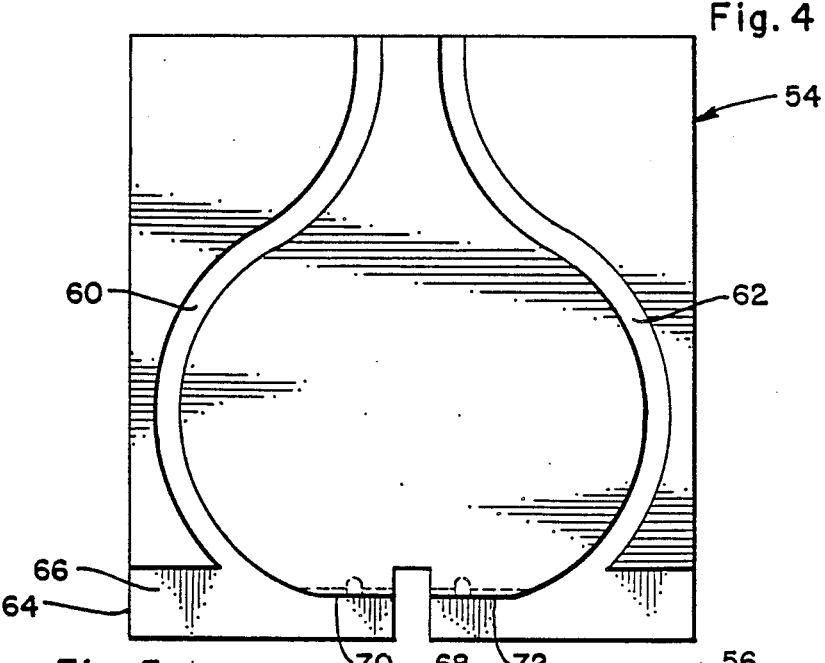
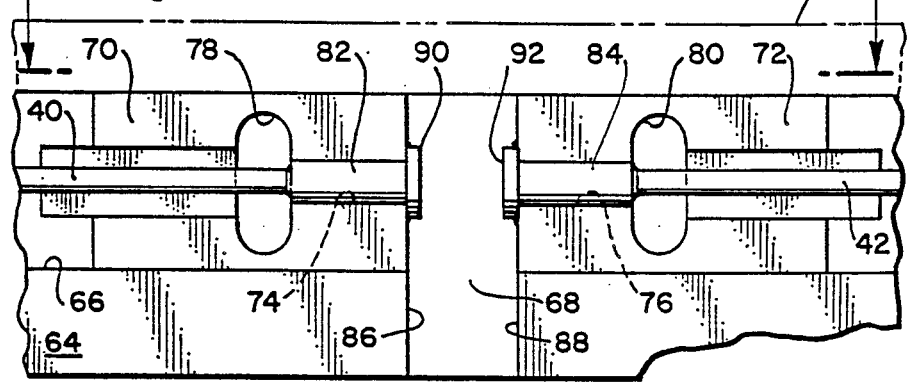
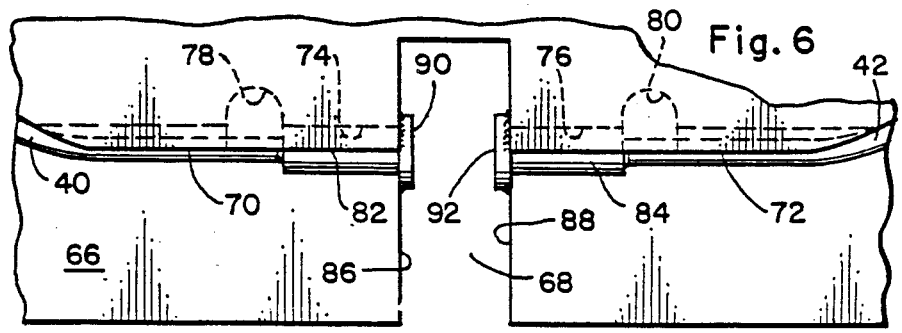

COLLIMATED LIGHT OPTRODE

FIELD OF THE INVENTION

This invention is directed to a collimated light optrode for the remote sensing of chemical species in solution by absorption spectroscopy.

BACKGROUND OF THE INVENTION

The apparatus and method described in Pesavento and Strawbridge U.S. Pat. No. 4,851,665 teach the manner in which absorption spectroscopy can be successfully used in the testing of chemical solutions, and particularly electroplating solutions. Work with the optrode taught in that patent has suggested means for optimizing the optrode. Other prior work is represented by a fiber optic luminescence measuring system taught in Brogardh U.S. Pat. No. 4,664,154. The present literature does not describe another system which utilizes a collimated light beam remote sensor to generate a signal for analysis by the absorption principle.

SUMMARY OF THE INVENTION

In order to aid in the understanding of this invention, it can be stated in essentially summary form that it is directed to a collimated light optrode system where light generated by an illumination source travels a fiber optic cable to the optrode which is immersed in the process flow to be analyzed. The optrode collimates the light beam before it crosses the sampling gap where it transects the process fluid to be analyzed. As it crosses the sampling gap, the light beam is absorbed in specific wavelength bands by the chemical species in solution. The collimated beam is then picked up by an opposing collimating lens in the optrode and transmitted to the analytical module via a second optical fiber.

It is thus a purpose and advantage of this invention to provide an improved collimated light optrode system for providing improved performance as an analytical instrument due to the ability to transmit more light, which improves the signal-to-noise ratio and increases the size of the portion of the process solution which can be sampled.

It is another purpose and advantage of this invention to produce a collimated light optrode system which is configured so as to be able to be inexpensively produced by the elimination of expensive components such as mirrored quartz prisms and sapphire lenses, and by ease of assembly.

Other purposes and advantages of this invention will become apparent from a study of the following portion of this specification, the claims and the attached drawings wherein:

BRIEF DESCRIPTION OF THE DRAWINGS

FIG. 4 is a plan of the optrode body with its cover removed, as seen generally along line 4—4 of FIG. 3.

FIG. 5 is an enlarged bottom view of the assembled optrode, with parts broken away.

FIG. 6 is a section taken generally along line 6—6 of FIG. 5, with parts broken away.

DESCRIPTION OF THE PREFERRED EMBODIMENT

Figure 1:
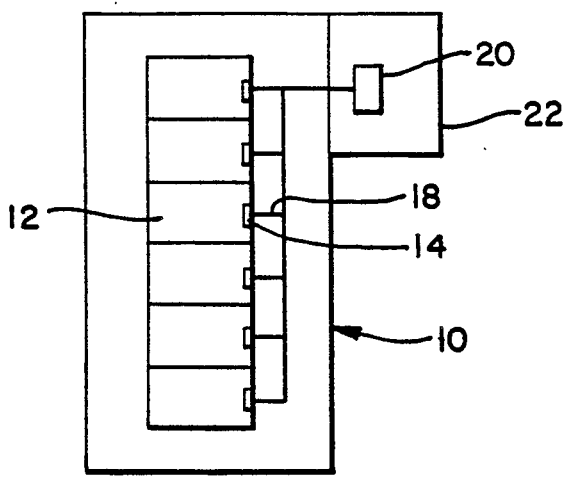
FIG. 1 is a diagrammatic view of a plating room showing the collimated light optrode system of this invention associated therewith for analysis of the plating tank solutions.
Figure 2:
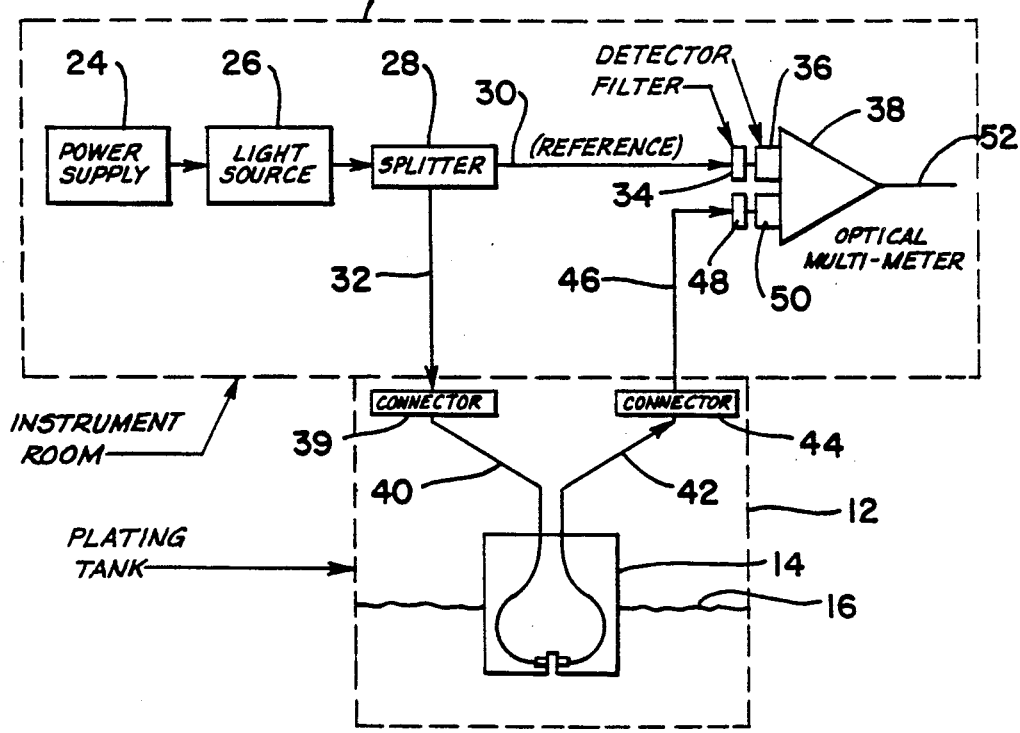
FIG. 2 is a schematic block diagram of the system.

FIG. 1 shows a plating room 10 with a plurality of plating tanks therein. One of the tanks is indicated at 12. The plating tanks are arranged for the plating of metal on various parts. The plating tanks may be for plating solder, lead, tin, copper, nickel, chromium, gold and other plating chemicals by electroplating methods. To analyze the process solution while plating occurs, an optrode 14 is suspended so that its lower end is in a plating solution 16, see FIG. 2. The optrode 14 is connected by a fiber optic link 18 to the analytical equipment 20 in room 22, which is protected from the plating area's corrosive environment and electrical and magnetic interference. This is schematically represented in FIG. 2. Each of the tanks for which analysis of the solution is required has its own optrode and is connected by a fiber optic link to the analytic equipment.

In FIG. 2, the analytic equipment is schematically shown as including power supply 24, which supplies power to light source 26. Light source 26 may be a white light or produce light in other more limited frequencies, as long as it has a substantial output in the wavelength of interest for the absorption of energy in accordance with the particular chemical of interest. Light from the light source goes to splitter 28, which produces a reference beam 30 and a sample beam 32. The beams may be of equal intensity, although in preferred practice, the reference beam has about 10 percent of the energy delivered into the splitter so that sample beam 32 has about 90 percent of the energy. The beam 30 passes through filter 34, if required by the light source and detector, which passes a narrow band of frequencies around the absorption frequency of interest. The output of filter 34 goes into detector 36, which is an optical-to-electronic transducer which serves as one input to comparator 38.

Reference beam 30 and sample beam 32 are in optical fibers. The fiber carrying sample beam 32 extends to connector 39. From the connector, the beam is conducted by fiber 40, which extends to and forms a part of optrode 14. More than one connector may be used if the run is long. In this way, the sample beam is transmitted to the optrode.

The signal beam is transmitted in fiber 42 through connector 44 and fiber 46 to filter 48, which again is a narrow band filter which substantially passes only the band of interest, and is preferably of the same spectral qualities as filter 34. Detector 50 converts the optical signal to an electronic signal and delivers the electronic signal to comparator 38. The fibers 40 and 42 make up the fiber optic link 18 from the optrode to the analytical equipment. The output 52 of comparator 38 provides a signal which indicates the concentration of the material in solution being analyzed.

One of the problems in printed circuit board manufacture is achieving and maintaining control over chemical species used in the electroplating processes. When control is not achieved and maintained, electroplating is of insufficient quality to provide printed circuit boards which will meet standards. As a specific example, in the copper electroplating process, copper ion, sulfate ion, and an organic additive must be maintained under strict quantitative control in the process fluid at all times. In the solder plate process, lead ion, tin ion, fluoborate ion and an organic additive must be maintained under strict control in the process fluid at all times. By optimizing the optrode, sensing sensitivity is improved.

Figure 3:
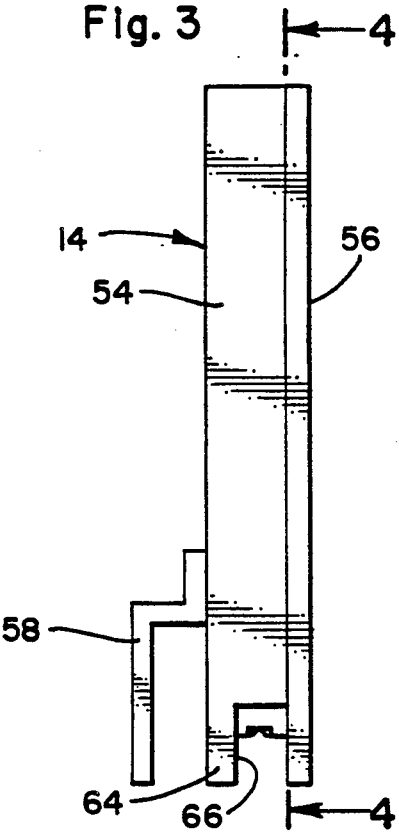
FIG. 3 is a side-elevational view of the collimated light optrode.

As seen in FIG. 3, optrode 14 includes a body 54 which carries a cover 56. Bracket 58 is attached to the body to permit the optrode to be engaged on a tank or elsewhere in the process stream to hold the lower edge of the optrode submerged in the process fluid. The body, with cover removed, is seen in FIG. 4. The body is configured with two curved channels 60 and 62 to respectively receive the fibers 40 and 42. At its lower edge, the body is cut away to leave a flange 64, which has a face 66 the same depth into the body as the channels. Notch 68 is cut into the body to form a gap as far as the upper edge of the flange 64, but the body between the channels 60 and 62 extends downward past the upper edge of the notch to a face 70 on the left side of the notch and 72 on the right side of the notch. The faces 70 and 72 are respectively cut with V-grooves 74 and 76. Also cut into the faces 70 and 72 are glue recesses 78 and 80.

GRIN (gradient index material) lenses 82 and 84 are adhesively secured into grooves 74 and 76, respectively, with their faces respectively even with the notch faces 86 and 88. The GRIN lenses which define the sample gap are protected by windows 90 and 92 made of sapphire or other suitable transparent material. The windows 90 and 92 are respectively adhesively secured in place over the GRIN (gradient index material) lenses. Fibers 40 and 42 are respectively bonded to the outer surfaces of the collimating GRIN lenses. When the assembly is complete, the grooves, except for notch 68, are filled with epoxy potting compound and the cover is put in place. A GRIN lens is a proprietary lens made of glass-like material which is progressively doped, radially so that it has a collimating function. The GRIN lens is available from Melles Griot, located at 1770 Kettering Street, Irvine, Calif. 92714. The gradient index lenses are manufactured by Nippon Sheet Glass Company of Japan and are marketed under the registered mark "Selfoc". Such lenses are produced by ion diffusion techniques which create a radial gradient index in a rod of glassy material. For a self-focusing lens, the refractive index of the rod varies parabolically as a function of radius. A major benefit of collimating, GRIN lenses is that it allows for easy assembly. The lens collects light that emerges in a wide angle from the fiber and focuses it into a narrow beam which passes through window 90, gap 68 and window 92 to the other collimating lens which receives the unabsorbed light and focuses it back into fiber optical cable 42. Alignment of the cable to the GRIN lenses is sensitive and must be properly done to optimize signal transmitted.

The body 54 and its cover 56 are made of a material which is resistant to the fluid in which the optrode is to be inserted. Synthetic polymer composition material is suitable for many liquids and is especially convenient for molding and/or machining. Vespel (available from duPont), polypropylene, and polyvinyl chloride are resistant to many acidic liquids and many other corrosive materials. The channels 60 and 62 are shaped so that they have parallel entries at the top of the body and the channels have curves in them which permit the optical fibers 40 and 42 lying therein to be brought to a face-to-face relationship on opposite sides of the notch 68. The curvature permits the multimode fibers to carry the signals from a parallel relationship to an axially coincident relationship so that the optical bends are conveniently achieved in the fiber rather than in mirrors or prisms. This construction orients the optical axis without involving other optical structures.

The improved performance of the optrode 14 is due to its ability to transmit at least three times more light than the previous structures. This provides a five to six decibel increase in system operating range and freedom from signal degradation caused by system noise. Equally important is increased sensitivity and accuracy of analytical results obtained because a larger portion of the process solution can be sampled in the gap. In addition to performance improvements, the structurally simple but more elegant design of the optrode yields very significant improvement in operating life, system reliability, fabrication cost, and component cost. Improved operational life and optrode reliability derive from the decreased risk of corrosive attack by the process solution. Basic departures from the previous design include the absence of mirrored prisms which are at risk from corrosive attack, absence of hemispheric lenses which require very precise positioning for focus, and the absence of a lens holder assembly which also requires precise alignment and might fail if process solution leaked into the structure. Manufacturing costs are considerably less because of the savings outlined above. The optrode 14 has proved to be effective for the analysis of copper ion and fluoroborate ion.

When the optrode is placed in solution, it operates on the principle of spectroscopic absorption. The specific chemical in the process fluid being sampled, that is occupying the gap formed by notch 68, absorbs light in a spectral band specific to the particular ion being analyzed. Light passing across the optrode gap will be absorbed in this wavelength region. As the concentration of this specific ion changes, the absorption effect changes in a consistent and predictable manner. Concentration changes thus result in detectable and measurable changes of light intensity which are quantified by the analytical module.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An optrode comprising:
   first and second optical fibers;
   a body having means for supporting said first and second optical fibers and for positioning their ends on a common axis;
   walls defining a gap in said body;
   first and second GRIN lenses for collimating light;
   means in said body adjacent said gap for supporting said first and second GRIN lenses on opposite sides of said gap in substantial axial alignment with each other, said first and second optical fibers being respectively attached to said GRIN lenses so that light transmitted in said first optical fiber and through said first GRIN lens is partially absorbed in liquid in said gap in accordance with the composition of material in said liquid in said gap so that the light in said second fiber contains information related to the liquid in said gap.

2. The optrode of claim 1 wherein said means for supporting said first and second optical fibers comprises first and second channels in said body, and there is a cover over said channels.

3. The optrode of claim 2 wherein said means for supporting said first and second GRIN lenses comprises first and second grooves in said body adjacent said gap and said GRIN lenses are secured in said grooves.

4. The optrode of claim 3 wherein said first and second optical fibers are respectively adhesively bonded to said first and second GRIN lenses.

5. An optrode comprising:
first and second optical fibers;
a body having first and second channels therein for supporting said first and second fibers and for positioning their ends on a common axis, a cover over said channels;
walls defining a gap in said body;
first and second GRIN lenses for collimating light;
first and second grooves in said body adjacent said gap, said first and second GRIN lenses being secured in said grooves on opposite sides of said gap in substantial axial alignment with each other, said first and second optical fibers being respectively adhesively attached to said GRIN lenses, said first and second GRIN lenses respectively having first and second fluid resistant windows positioned thereover to protect said lenses from fluid in which said optrode is immersed so that light transmitted in said first optical fiber and through said first GRIN lens is partially absorbed in liquid in said gap in accordance with the composition of material in said liquid in said gap so that the light in said second fiber contains information related to the liquid in said gap.

6. An optrode comprising:
first and second optical fibers;
a body having means for supporting said first and second optical fibers and for positioning their ends on a common axis;
walls defining a gap in said body;
first and second GRIN lenses for collimating light;
means in said body adjacent said gap for supporting said first and second GRIN lenses on opposite sides of said gap in substantial axial alignment with each other, said first and second optical fibers being respectively attached to said GRIN lenses, said first and second GRIN lenses respectively have first and second fluid resistant windows positioned thereover to protect said lenses from fluid in which said optrode is immersed so that said light transmitted in said first optical fiber and through said first GRIN lens is partially absorbed in liquid in said gap in accordance with the composition of material in said liquid in said gap so that the light in said second fiber contains information related to the liquid in said gap.

7. The optrode of claim 6 wherein said means for supporting said first and second GRIN lenses comprises first and second grooves in said body adjacent said gap and said GRIN lenses are secured in said grooves.

8. The optrode of claim 7 wherein there is a power supply and a light source together with an optical beam splitter, said power supply being connected to said light source and said light source supplying light to said beam splitter, said beam splitter having a reference output beam and a sample beam, said sample beam being connected to said first optical fiber, said equipment including a comparator, said reference beam being connected to said comparator and said second fiber being connected to said comparator so that said comparator indicates absorption of the light in said second fiber.

9. The optrode of claim 8 wherein said comparator is in a compartment protected from corrosive action and said optrode is at a plating tank.

10. The optrode of claim 9 wherein said reference beam is connected to pass through a first filter and to a detector which is connected to said comparator and said signal beam in said second fiber is connected to pass through a second filter and a second detector which is connected to said comparator.

11. An optrode comprising:
first and second optical fibers;
a body having means for supporting said first and second optical fibers and for positioning their ends on a common axis;
walls defining a gap in said body;
first and second GRIN lenses for collimating light;
means in said body adjacent said gap for supporting said first and second GRIN lenses on opposite sides of said gap in substantial axial alignment with each other, said first and second optical fibers being respectively attached to said GRIN lenses, a power supply, and a light source together with an optical beam splitter, said power supply being connected to power said light source and said light source supplying light to said beam splitter, said beam splitter having a reference output beam and a sample beam, said sample beam being connected to said first optical fiber, a comparator, said reference beam being connected to said comparator and said second fiber being connected to said comparator to indicate absorption in light between said first and said second fiber so that light transmitted in said first optical fiber and through said first GRIN lens is partially absorbed in liquid in said gap in accordance with the composition of material in said liquid in said gap so that the light in said second fiber contains information related to the liquid in said gap.

12. The optrode of claim 11 wherein said comparator is in an environment protected from corrosive action and said optrode is at a plating tank.

13. The optrode of claim 12 wherein said reference beam is connected to pass through a first filter and to a detector which is connected to said comparator and said signal beam in said second fiber is connected to pass through a second filter and a second detector which is connected to said comparator.

14. An optrode comprising:
a body, said body having a top portion and a bottom portion, said body having a face surface;
first and second channels formed in said body and extending to said face surface;
first and second optical fibers respectively lying in said first and second channels, said channels being shaped so that said optical fibers enter the top portion of said body and are directed substantially axially toward each other in the bottom portion of said body, with said channels having sufficiently large bend radii as to receive said optical fibers without damage;
walls defining a notch in said body, said body having an aligned groove extending across said notch;
first and second GRIN lenses lying in said groove on opposite sides of said notch;

said first and second optical fibers respectively being optically connected to said first and second GRIN lenses;

a cover over said channels; and potting compound in said channels and covering said optical fibers to protect said fibers, potting compound on said GRIN lenses to protect said GRIN lenses within said optrode.

15. The optrode of claim 14 further including first and second transparent protective windows respectively secured in said notch over said first and second GRIN lenses to protect the faces of said GRIN lenses adjacent said notch.

16. The optrode of claim 15 further including at least one plating tank and means for positioning said optrode so as to have its notch immersed in plating tank liquid;

a light source for connection to said first fiber;

a compartment protected from corrosive action, a sensor in said protected compartment, said second fiber being connected to said sensor so that liquid in said notch in said optrode affects the light in said second optical fiber so that said sensor indicates constituents of the liquid.

17. The optrode of claim 16 further including a reference beam from said light source to said sensor and said sensor is a comparator to compare said reference beam to the light in said second fiber.

18. The optrode of claim 15 wherein said body and said cover are made of synthetic polymer composition material.

19. The optrode of claim 18 wherein said channels in said body are substantially upright and parallel to each other at the top of said body so that said first and second fibers enter the top of said body.

20. The optrode of claim 19 further including a bracket on said body for holding .said body in position with said notch immersed in plating liquid.

* * * * *